US00PP10885P

United States Patent [19]

Roberson

[11] Patent Number: Plant 10,885

[45] Date of Patent: May 4, 1999

[54] LANTANA PLANT NAMED 'ROBPATSUN'

[76] Inventor: Robert J. Roberson, 31706 E. Pink Hill Rd., Grain Valley, Jackson County, Mo. 64029

[21] Appl. No.: 08/841,310

[22] Filed: Apr. 30, 1997

[51] Int. Cl.[6] ..... A01H 5/00

[52] U.S. Cl. ..... Plt./227

[58] Field of Search ..... Plt./54.1, 227

*Primary Examiner*—Howard J. Locker
*Assistant Examiner*—Kent L. Bell
*Attorney, Agent, or Firm*—Rothwell, Figg, Ernst & Kurz

[57] ABSTRACT

This invention relates to a new and distinct *Lantana camara* cultivar which is outstanding because of its: 1) rapid, dependable growth habit; 2) its bright lemon-colored florets; 3) its dense prostrate growth habit with medium internode spaces; 4) its slow tendency to set seed; 5) its prolific blooming habit; and 6) its ease of vegetative propagation.

1 Drawing Sheet

SUMMARY OF THE INVENTION

This invention relates to a new and distinct *Lantana camara* cultivar which is outstanding because of its 1) rapid, dependable growth habit; 2) its bright lemon-colored florets; 3) its dense prostrate growth habit with medium internode spaces; 4) its slow tendency to set seed; 5) its prolific blooming habit; 6) and its ease of vegetative propagation. The claimed *Lantana camara* plant was primarily selected for these characteristics. This selection was made from a specially designed Lantana hybridizing program with said hybrid cultivars being planted and grown in Grain Valley, Mo.

ORIGIN AND ASEXUAL REPRODUCTION

Asexual reproduction of this cultivar by tip cuttings was directed by me, such reproduction establishing that the plant does in fact maintain the characteristics described, in successive generations.

It should be noted that the plant was initially selected from a Lantana planting being grown near Grain Valley, Mo. in a cultivated area and has since been reproduced by tip cuttings in the vicinity of Grain Valley, Mo. with the new and distinct characteristics stated herein, found to be maintained through successive generations as before recited.

*Lantana camara* is native to the subtropics and tropical North and South America. They are woody ornamentals which are not usually winter hardy North of USDA horticulture Zone 9. The roughish leaves range from yellow-green to green to blue-green and the two basic growth forms are mounding and trailing (weeping). Bloom color usually include yellow, white, cream, pink, or orange.

The cultivar of *Lantana camara* 'Robpatsun' may further be described as having a number of distinctive characteristics which are enumerated in the succeeding specific description but broadly stated as comprising; 1) rapid, dependable growth habit; 2) bright lemon-colored florets; 3) dense prostrate growth habit with medium internode spaces; 4) slow tendency to set seed; 5) prolific blooming habit; 6) and ease of vegetative propagation. I have chosen to identify this new cultivar as *Lantana camara* 'Robpatsun'. This cultivar is being marketed in the United States under the name of Patriot (tm) 'Sunburst'.

BRIEF DESCRIPTION OF THE DRAWING

The accompanying photograph shows as nearly true as it is reasonably possible to make the same, in color illustrations of this character, typical leaves and flowers of the new variety.

DETAILED DESCRIPTION

Figure 1:
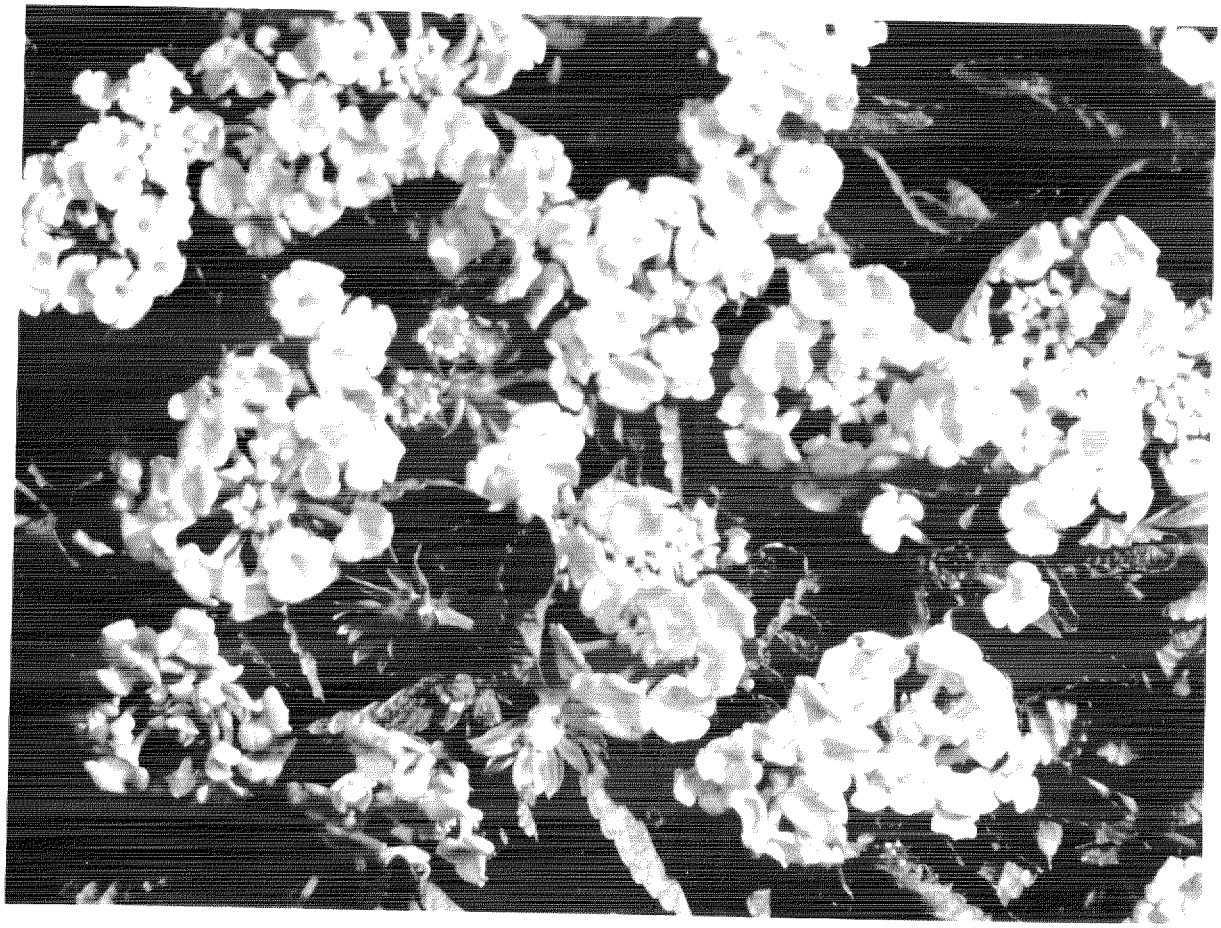
FIG. 1 illustrates the flower form and color and leaf color.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo.

Parentage:

*Seed parent.*—*Lantana camara* Patriot(tm) 'Moonshine' (in a semi-controlled open pollination).

*Pollen parent.*—Unknown.

Propagation: Asexual reproduction by tip cuttings started near Grain Valley, Mo.

Plant descriptions:

*Inflorescence and reproductive parts.*—The inflorescence is a flat topped round cluster of 25–30 florets. The individual clusters are determinate and arise from the leaf axils. Each individual floret is slightly un-symmetrical with a bilateral symmetry and is subtended by a single bract. The perianth consist of: the Calyx (5 united sepals) and the Corolla (5 united petals with a narrow tube). The flowers are zygomorphic, hermaphroditic, and have 4 introse stamens which are didynamous. The ovary is superior, the style is terminal, and the stigma is lobed. The ovary is 2 locular, but is divided into 4 loculi by a false septum in each loculus. The placentation is axile with 2 ovules per carpel.

The fruit classification is drupe and potentially contains 2 seeds. When fruit forms, it is olive green (PMS#377); then matures through a darker green (PMS#385) to a near black (PMS#439).

Inflorescence dimensions:

*Bloom cluster.*—1.1" in diameter.

*Single floret.*—0.2".

*Pedicle length.*—1.2".

*Corolla tube.*—0.4".

Inflorescence colors:

*Bud.*—Canary Yellow (PMS#102).

*First opening.*—Pantone Yellow (Process).

*Maturity.*—Yellow (PMS#107).

*Tube.*—Process Yellow.

Developmental pattern: First flowers develop in a circular pattern on the periphery of the inflorescence.

Branching: 'Robpatsun' self-branches at each node and the internode spaces are about 1.6 inches. Florets are formed at each node giving the overall appearance of the plant a 20% more dense leaf and floral presentation relative to many other *Lantana camara*'s such as Patriot 'Firewagon' (unpatented) and 'Robpatdes' (U.S. Plant Pat. No. 10,156). This plant does not require pinching to obtain density.

Height and spread: In one growing season, i.e., frost to frost (May 5 to September 28, in USDA zone 5) Robpatsun reaches a height of 1 foot by 3 feet wide.

Plant vigor: Newly rooted (two week old) tip cuttings maintained in a greenhouse at 70° F. night temperature and 85° F. day temperature with 16 hour full sun days will result in an average growth of 9/10 of one inch per week.

Leaves and stems:

*Leaf shape.*—Ovate.

*Leaf margins.*—Serrate.

*Leaf tip and base.*—Acute.

*Leaf veins.*—Pinnate.

*Leaf surface.*—Rough due to bristly hairs.

*Leaf arrangement.*—Opposite.

*Leaf color.*—Immature leaves are medium light green (PMS #370) and mature leaves are medium green (PMS #364).

*Leaf size.*—Length 1.25". Petiole 0.22". Width 0.9".

*Stem.*—Square in youth becoming round and woody with age.

Roots: Highly branched and fibrous.

Flowering time: The color display begins blooming at 6–7 weeks after cuttings are made, or 4 weeks after potting, and continue until temperatures drop below 45 degrees Fahrenheit.

Diseases: No unusual susceptibility to diseases noted to date.

Insects: Typical of this plant genus, white flies can be attracted to Lantana. There are no other insect problems known at this time.

General Observations

*Lantana camara* 'Robpatsun', with its 1) rapid, dependable growth habit; 2) bright lemon-colored florets; 3) dense prostrate growth habit with medium internode spaces; 4) slow tendency to set seed; 5) prolific blooming habit; 6) and its ease of propagation is an improved cultivar in the yellow Lantana color ranges available in today's horticulture market.

For the purpose of ornamental horitculture in our present living environments which include smaller yards and patio gardening, *Lantana camara* plant 'Robpatsun' is ideal due to several characteristics:

A. It is an excellent plant for mass planted ground covers, low borders, hanging baskets or focal display containers. *Lantana camara* 'Robpatsun' will produce a continuous display of bright, lemon yellow throughout the summer. This plant remains in bloom when most other flowering perennials' seasons have ended.

B. The prolific blooming tendency and dense growth habit of this cultivar, with its medium internode spaces provides the garden or landscape with a "fuller", more dense presentation of both foliage and bloom florets; thus making a more dramatic color statement than the average Lantana.

C. This cultivar's slow tendency to set seed allows more continual blooming, and a maintenance of optimum color beauty. This characteristic of being slow to set seed also provides the garden or landscape with a clean environment free of unwanted seedlings.

D. The ease of propagation of 'Robpatsun' makes this Lantana a very commercially viable product to serve the horticulture industry.

Comparison to Known Varieties

*Lantana camara* plant 'Robpatsun' should be compared with *Lantana camara* 'New Gold' (unpatented) as this is the best color comparison known in today's trade. The points of comparison are: a) the bright yellow color of 'Robpatsun' has greater visual carrying power than the yellow-gold color of 'New Gold'; b) the semi-compact growth habit of 'Robpatsun' is more manageable in the landscape than 'New Gold' and provides more color or bloom dominance in the planting; c) 'Robpatsun' allows a cleaner landscape or garden than 'New Gold' because it is slower to set seed.

'Robpatsun' is less gold and more yellow than 'Moonshine' (unpatented). Robpatsun's yellow has less red which gives a more vibrant yellow for landscaping.

I claim:

1. The new and distinct cultivar of *Lantana camara* plant substantially as illustrated and described.

* * * * *